(12) United States Patent
Baril et al.

(10) Patent No.: US 11,534,258 B2
(45) Date of Patent: Dec. 27, 2022

(54) CUTTING GUARD

(71) Applicant: Covidien LP, Mansfield, MA (US)

(72) Inventors: Jacob C. Baril, Norwalk, CT (US);
Jason T. Mickus, Avon, CT (US);
Saumya Banerjee, Hamden, CT (US)

(73) Assignee: COVIDIEN LP, Mansfield, MA (US)

( * ) Notice: Subject to any disclaimer, the term of this patent is extended or adjusted under 35 U.S.C. 154(b) by 183 days.

(21) Appl. No.: 17/003,933

(22) Filed: Aug. 26, 2020

(65) Prior Publication Data

US 2022/0061952 A1 Mar. 3, 2022

(51) Int. Cl.
| | |
|---|---|
| *A61B 17/02* | (2006.01) |
| *A61B 90/00* | (2016.01) |
| *A61B 17/34* | (2006.01) |
| *A61B 17/32* | (2006.01) |

(52) U.S. Cl.
CPC .......... *A61B 90/08* (2016.02); *A61B 17/0293* (2013.01); *A61B 17/320016* (2013.01); *A61B 17/3423* (2013.01); *A61B 2090/08021* (2016.02)

(58) Field of Classification Search
CPC . A61B 17/02; A61B 17/0218; A61B 17/0293; A61B 17/3423
See application file for complete search history.

(56) References Cited

U.S. PATENT DOCUMENTS

| | | | |
|---|---|---|---|
| 5,578,000 A | 11/1996 | Greff et al. | |
| 5,941,873 A | 8/1999 | Korenfeld | |
| 6,033,362 A | 3/2000 | Cohn | |
| 6,544,210 B1 | 4/2003 | Trudel et al. | |
| 7,789,946 B2 | 9/2010 | Schultz et al. | |
| 7,901,353 B2 | 3/2011 | Vayser et al. | |
| 9,427,288 B1 | 8/2016 | Chenger et al. | |
| 10,076,358 B2 * | 9/2018 | Zergiebel | A61B 17/0218 |
| 2005/0054993 A1 | 3/2005 | Falahee | |
| 2006/0247673 A1 * | 11/2006 | Voegele | A61B 17/4241 606/191 |
| 2012/0089093 A1 | 4/2012 | Trusty | |
| 2013/0184536 A1 | 7/2013 | Shibley et al. | |
| 2014/0330285 A1 | 11/2014 | Rosenblatt et al. | |
| 2016/0158468 A1 | 6/2016 | Tang et al. | |
| 2017/0049427 A1 | 2/2017 | Do et al. | |

(Continued)

*Primary Examiner* — Si Ming Ku
(74) *Attorney, Agent, or Firm* — Carter, DeLuca & Farrell LLP (57) ABSTRACT

A tissue guard for use with a surgical access device includes an upper portion having: a proximal ring with proximal and distal ends, the distal end having a first mechanical interface disposed therearound; a plurality of fingers extending about the proximal ring that the access device; an inner peripheral surface having an upper channel; and a plurality of second mechanical interfaces disposed about a distal end of the inner peripheral surface. The lower portion includes: a body having a proximal end including a corresponding first mechanical interface disposed therearound configured to engage the first mechanical interface of the upper portion; a lower channel defined within the body including a plurality of corresponding second mechanical interfaces configured to engage the plurality of second mechanical interfaces of the upper portion; and long and short petals disposed of the lower portion to facilitate insertion of the tissue guard within an incision.

20 Claims, 9 Drawing Sheets

(56) References Cited

U.S. PATENT DOCUMENTS

2017/0325657 A1 11/2017 Prior
2018/0008250 A1 1/2018 Joseph
2018/0049771 A1 2/2018 Rhemrev-Pieters

* cited by examiner

CUTTING GUARD

FIELD

The present disclosure relates to tissue specimen removal and, more particularly, to surgical access devices, tissue guards and systems incorporating the same for use in tissue specimen removal procedures and other surgical procedures.

BACKGROUND

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to facilitate removal from the internal body cavity. Typically, a surgical sleeve and a specimen containment bag are used for this purpose. Moreover, during specimen rescission, smoke may cloud the operating site and may require evacuation therefrom. Smoke evacuation systems are commonplace for use with the surgical sleeve.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a tissue guard for use with a surgical access device that includes an upper portion having: a proximal ring including proximal and distal ends, the distal end including a first mechanical interface disposed therearound; a plurality of fingers extending about the proximal ring, each finger configured to mechanically engage a rim of an access device to secure the tissue guard thereon; an inner peripheral surface having an upper channel defined therein disposed in fluid communication with an operating cavity, the inner peripheral surface depending from the proximal ring; and a plurality of second mechanical interfaces disposed about a distal end of the inner peripheral surface. The lower portion includes: an elongated body having proximal and distal ends, the proximal end including a corresponding first mechanical interface disposed therearound configured to, upon assembly, mechanically engage the first mechanical interface of the upper portion; a lower channel defined in the elongated body in vertical registration with the upper channel, the lower channel including a plurality of corresponding second mechanical interfaces disposed thereon configured to, upon assembly, engage the plurality of second mechanical interfaces of the upper portion; and a long petal and a short petal disposed at the distal end of the lower portion, the short petal configured to move between a first position wherein the short petal is disposed within the lower channel to facilitate insertion of the long petal within an incision and a second position wherein the short petal is extended relative to the lower channel and in substantial opposition to the long petal to facilitate retention of the tissue guard within the incision.

In aspects according to the present disclosure, the first mechanical interface of the upper portion includes a tongue and groove and the first mechanical interface of the lower portion includes a tongue and groove configured to mechanically engage the tongue and groove of the upper portion. In other aspects according to the present disclosure, the plurality second mechanical interfaces of the upper portion includes a male post snap and the plurality second mechanical interfaces of the lower portion includes a female post snap configured to mechanically engage the plurality of male post snaps of the upper portion.

In aspects according to the present disclosure, each of the plurality of fingers of the upper portion includes a flange at a distal end thereof configured to engage an underside of the rim of the access device. In other aspects according to the present disclosure, each flange of the plurality of fingers is disposed at an angle relative to each finger. In yet other aspects according to the present disclosure, each flange of the plurality of fingers is disposed at an angle in the range of about 60 degrees to about 80 degrees relative to each finger.

In aspects according to the present disclosure, the short petal is selectively invertable within the lower channel. In other aspects according to the present disclosure, the long petal is shaped like a shoe horn and is configured to pry the incision open upon insertion therein. In yet other aspects according to the present disclosure, after insertion of the long petal within the incision, the short petal is selectively extendible from the lower channel to engage tissue opposite the long petal to facilitate retention of the tissue guard.

Provided in accordance with aspects of the present disclosure is a tissue guard for use with a surgical access device that includes an upper portion having: a proximal ring including proximal and distal ends, the distal end including a first mechanical interface disposed therearound; a plurality of fingers extending about the proximal ring, each finger configured to mechanically engage an underside of a rim of an access device to secure the tissue guard thereon; an inner peripheral surface having an upper channel defined therein disposed in fluid communication with an operating cavity, the inner peripheral surface depending from the proximal ring; and a plurality of second mechanical interfaces disposed about a distal end of the inner peripheral surface. The lower portion includes: an elongated body having proximal and distal ends, the proximal end including a corresponding first mechanical interface disposed therearound configured to, upon assembly, mechanically engage the first mechanical interface of the upper portion; and a lower channel defined in the elongated body in vertical registration with the upper channel, the lower channel including a plurality of corresponding second mechanical interfaces disposed thereon configured to, upon assembly, engage the plurality of second mechanical interfaces of the upper portion, wherein the lower portion is configured for initial insertion within the access device and upper portion is subsequently engaged with the lower portion.

In aspects according to the present disclosure, the first and second mechanical interfaces of the upper and lower portions are configured to engage in a substantially simultaneous manner. In other aspects according to the present disclosure, the first and second mechanical interfaces of the upper and lower portions are configured to engage in a sequential manner. In yet other aspects according to the present disclosure, the first and second mechanical interfaces of the upper and lower portions are configured to engage one another prior to engagement of the plurality of fingers of the upper portion with the access device.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1A:
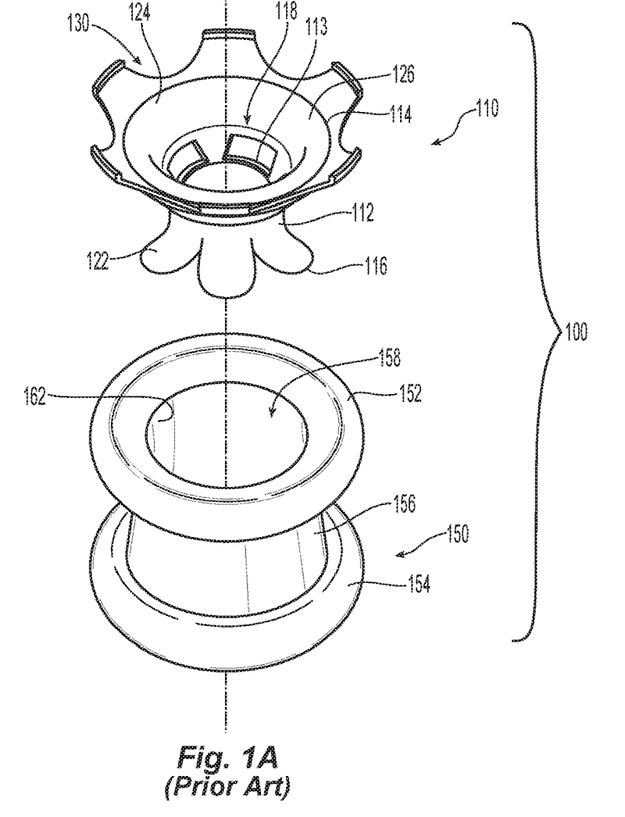
FIG. 1A is an exploded, top, perspective view of a prior art system including an access device and a tissue guard.
Figure 1B:
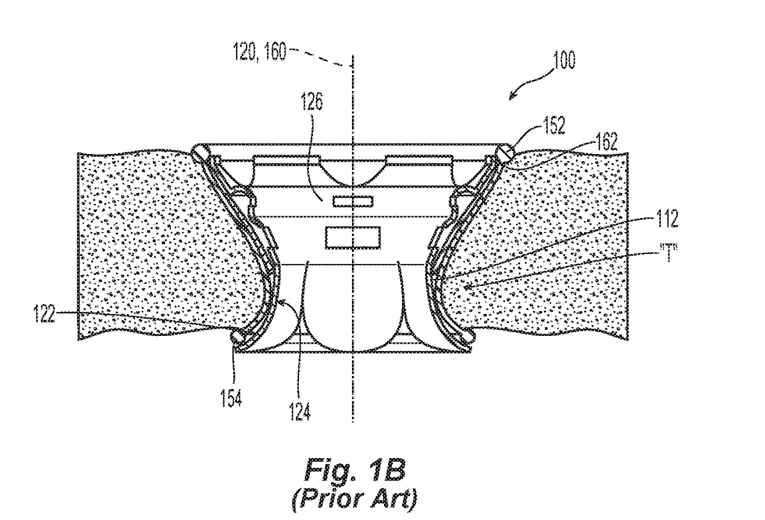
FIG. 1B is a cross-sectional view of the prior art system of FIG. 1A disposed within an opening in tissue.

Turning to FIGS. 1A and 1B, a prior art system 100 provided in accordance with the present disclosure includes a tissue guard 110 and an access device 150. Tissue guard 110 is monolithically formed as a single piece of material, e.g., a biocompatible plastic such as, for example, polyethylene, polycarbonate, etc., from any suitable method, e.g., injection molding. The material, thickness, and configuration of tissue guard 110 are such that tissue guard 110 defines sufficient stiffness to maintain its shape when positioned within an opening in tissue "T" and/or when engaged within access device 150. However, the material, thickness, and configuration of tissue guard 110 also provide sufficient resilient flexibility to permit manipulation of tissue guard 110 from an at-rest position for insertion into an opening in tissue "T" and/or for engagement within access device 150, with tissue guard 110 returning to or towards the at-rest position after insertion and/or engagement as explained in more detail below. Further, the material, thickness, and configuration of tissue guard 110 is selected such that tissue guard 110 is configured to withstand cutting and puncturing by surgical knives, scalpels, pencils, and the like, thereby protecting surrounding tissue "T" and/or access device 150 from being cut or punctured. Tissue guard 110 may additionally or alternatively be configured to inhibit transfer of thermal and/or electrical energy therethrough to protect surrounding tissue "T" and/or access device 150 from thermal and/or electrical energy.

Continuing with reference to FIGS. 1A and 1B, tissue guard 110 includes a body 112 defining an open proximal end 114, an open distal end 116, and a lumen 118 extending therethrough between open proximal and distal ends 114, 116, respectively. Lumen 118 defines a longitudinal axis 120 and is configured to receive one or more surgical instruments (not shown) therethrough. In embodiments, body 112 defines a funnel-shaped configuration wherein a diameter of body 112 at open proximal end 114 thereof is greater than a diameter of body 112 at open distal end 116 thereof. Additionally or alternatively, the exterior surface 122 of body 112 may define a generally concave configuration while the interior surface 124 of body 112, which defines lumen 118, may define a generally convex configuration.

Access device 150 may be configured as a tissue retractor, an access port, or other suitable access device configured for positioning within an opening in tissue "T," e.g., a surgical incision or a naturally-occurring orifice, to provide access therethrough into an internal surgical site. Access device 150 includes a proximal rim 152 configured for positioning on an external side of the opening in tissue "T," a distal rim 154 configured for positioning on an internal side of the opening in tissue "T," and a body 156 extending between proximal and distal rims 152, 154, respectively. Body 156 is configured to extend through the opening in tissue "T" and defines a passageway 158 extending longitudinally therethrough to permit access to an internal surgical site through the opening in tissue "T." Passageway 158 defines a longitudinal axis 160. At least a portion of body 156 of access device 150 may be flexible to facilitate insertion and positioning of access device 150 within the opening in tissue "T." In embodiments, body 156 is formed from a flexible sleeve of material including one or more layers of material. Further, access device 150 may be selectively adjustable, e.g., by rolling proximal rim 154 distally about body 156, to retract tissue "T" and/or secure access device 150 within the opening in tissue "T." Access device 150 may further define an inwardly-extending overhang 162 between proximal rim 154 and body 156 and extending annularly about passageway 158.

As shown in FIG. 1B, in use, access device 150 is positioned within an opening in tissue "T" such that, as noted above, distal rim 154 is disposed on an internal surface of tissue "T" on the internal side of the opening in tissue "T," body 156 extends through the opening in tissue "T," and proximal rim 152 is disposed on an exterior surface of tissue "T" on the external side of the opening in tissue "T." As also noted above, access device 150 may be adjusted to conform access device 150 to a patient's anatomy, retracting tissue "T" and/or securing access device 150 within the opening in tissue "T." With access device 150 disposed within the opening in tissue "T," tissue guard 110, led by open distal end 116 thereof, is inserted into passageway 158.

Figure 1C:
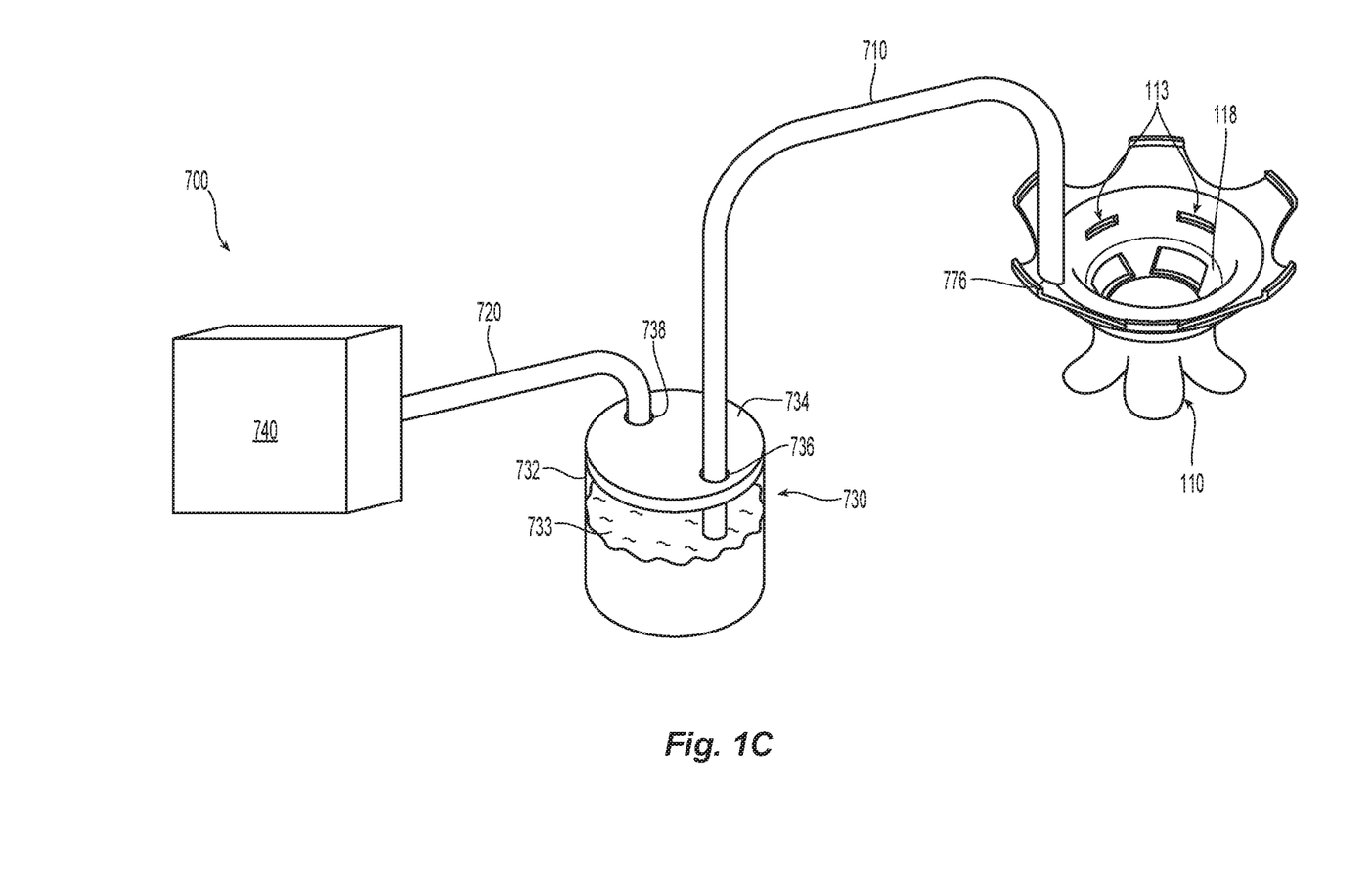
FIG. 1C is a schematic illustration of a smoke evacuation system for use with one or more of the access devices and tissue guards described herein.

Turning to FIG. 1C, smoke evacuation system 700 is provided in accordance with the present disclosure and is shown generally including tissue guard 110, tubing 710, 720, a collection reservoir 730, and a smoke evacuation (or vacuum) source 740. The various tissue guards disclosed herein are all designed to work with system 700. Tissue guard 110 and tubing 710 are detailed above and are coupled to one another, e.g., via engagement of one end of tubing 710 about exhaust connection 776 of tissue guard 710. The other end of tubing 710 extends into collection reservoir 730 in sealing relation therewith.

Collection reservoir 730 includes a base 732 and a lid 734 sealed about base 732. Lid 734 defines first and second ports 736, 738 configured to receive ends of tubing 710, 720, respectively, in sealing relation therewith. These ends of tubing 710, 720 extend into the interior volume 733 of base 732 and are spaced-apart from one another as well as the bottom of base 732. Tubing 720 extends from collection reservoir 730 to smoke evacuation source 740 wherein the other end of tubing 720 is coupled to smoke evacuation source 740. In this manner, upon activation of smoke evacuation source 740, suction is established through lip 126 of tissue guard 110, tubing 710, collection reservoir 730, tubing 720, to smoke evacuation source 740. During use, this suction, in addition to evacuating smoke from tissue guard 110, may also suction liquids, tissue, and/or debris through tubing 710. However, as a result of the ends of tubing 710, 720 being spaced-apart from one another within collection reservoir 730 and spaced-apart from the bottom of base 732 of collection reservoir 730, the liquids, tissue, and/or debris are suctioned into collection reservoir 730 and deposited therein, while only the smoke and other gaseous fluids are further suctioned from collection reservoir 730 through tubing 720 to smoke evacuation source 740. As such, smoke evacuation source 740 is protected by inhibiting suctioning of liquids, tissue, and/or debris into smoke evacuation source 740.

Figure 2A:
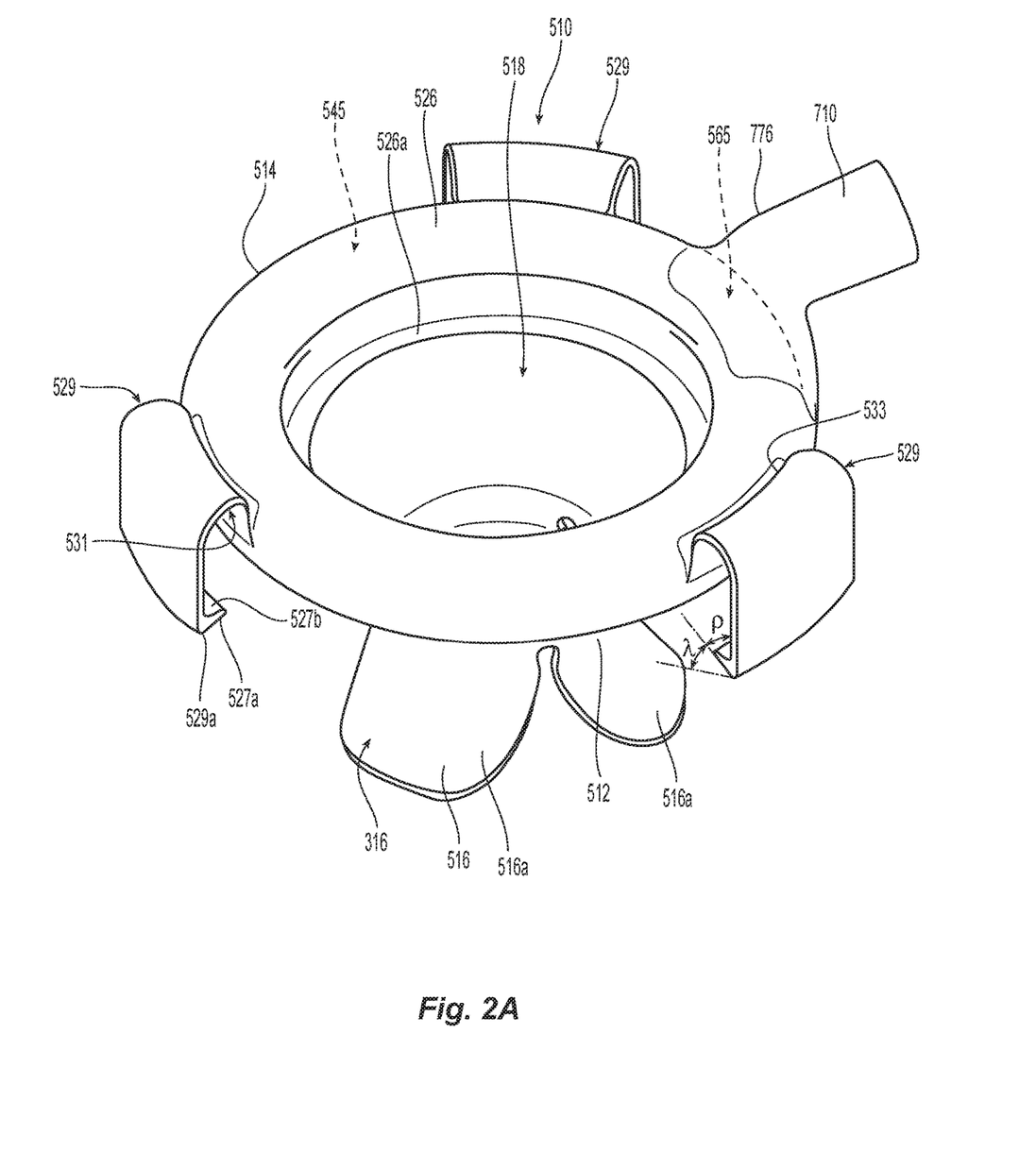
FIG. 2A is a top perspective view of a tissue guard for use with the access device.
Figure 2B:
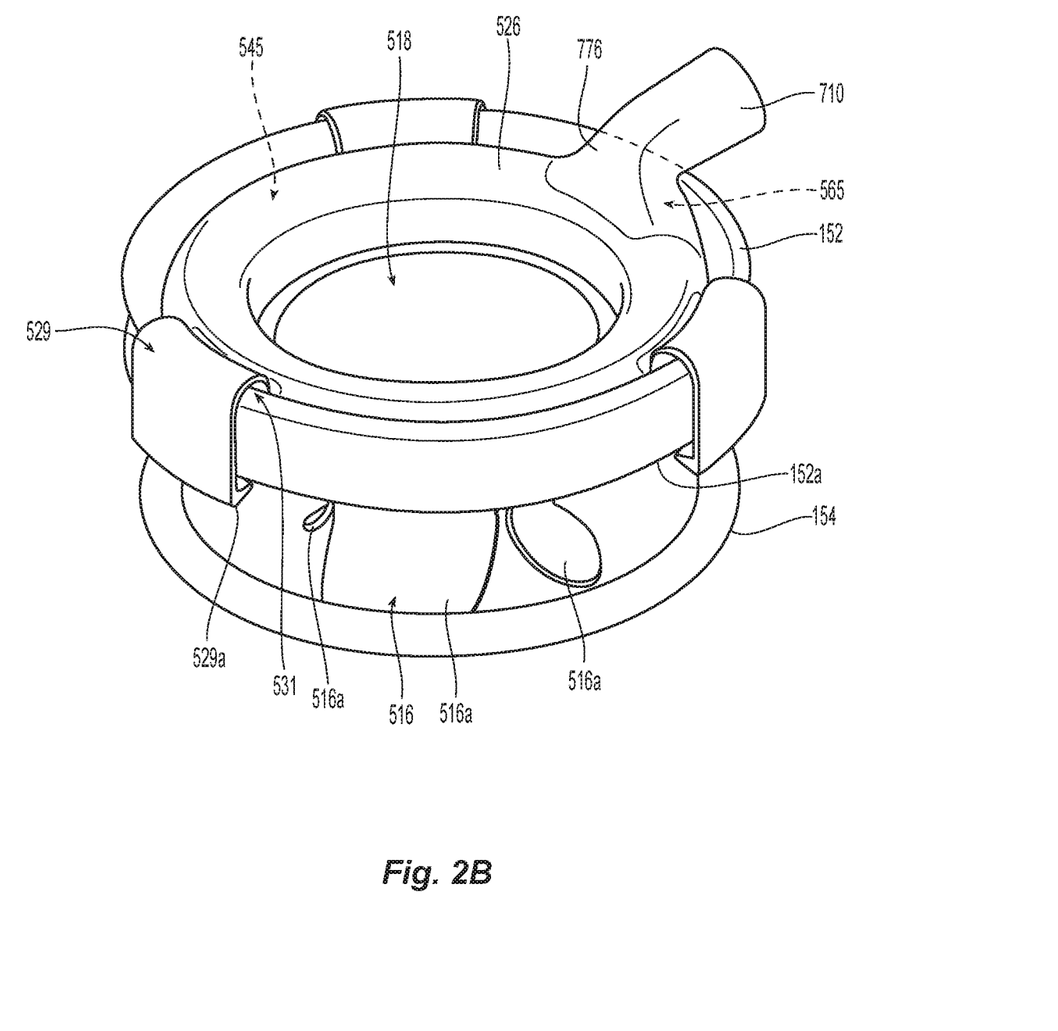
FIG. 2B is a top perspective view of the tissue guard of FIG. 2A engaged to a proximal rim of the access device.

Turning to FIGS. 2A-2B, another tissue guard 510 provided in accordance with the present disclosure is shown. Tissue guard 510 is similar to tissue guard 110 except as explicitly contradicted below and may be used in conjunction with access device 150 as part of a system similar to system 100. For purposes of brevity, only differences between tissue guard 510 and tissue guard 110 are detailed below, while similarities are summarily described or omitted.

Tissue guard 510 includes a body 512 defining an open proximal end 514, an open distal end 516, and a lumen 518 extending therebetween. A lip 526 extends radially outwardly from open proximal end 514 of body 512 and includes a plurality of fingers 529 extending from an outer peripheral surface thereof. The fingers 529 may be equidistantly-spaced about the lip 526 or may be spaced in any particular manner depending upon a particular purpose. In embodiments, a continuous finger (not shown) may be annularly spaced about the lip 526.

Each finger 529 includes an arcuate channel 531 defined along an inner peripheral surface thereof configured to at least partially encapsulate or mount atop rim 152 of the access device 150. More particularly, when the tissue guard 510 is first inserted into access device 150, channel 531 of each finger 529 aligns atop rim 152 of access device 150 and is poised for engagement atop rim 152 when the fingers 529 are secured. Each finger 529 also includes a flange 529a disposed at a distal end thereof that is configured to engage an underside of rim 152 to secure the tissue guard 510 in place. Finger 529 is configured to flex upon adaption of the tissue guard 510 onto access device 150 by virtue of rim 152 forcing flange 529a and finger 529 outwardly as the tissue guard 510 is inserted. Upon full insertion of the tissue guard 510 atop and into access device 150, the channel 531 of finger 529 encapsulates the rim 152 while the flange 529a snaps into place under rim 152 thereby locking the tissue guard 510 atop access device 150. The finger 529 is biased in the locked position. The flange 529a extends inwardly relative to the proximal ring 152 and operably engages the underside of the proximal ring 152 when biased.

Flange 529a may be angled to both facilitate insertion and to facilitate engagement. More particularly, an outer peripheral surface 527a of flange 529a may be disposed at a first angle lamda ($\lambda$) in the range from about 45 degrees to about 60 degrees to encourage the finger 529 and, hence, the tissue guard 510, to slip into lumen 118 and an inner peripheral surface 527b is disposed at second angle phi ($\varphi$) in the range from about 60 degrees to about 80 degrees to facilitate engagement of flange 129a with the underside of rim 152. The shape of channel 531 may be dimensioned to conform to the shape of the outer peripheral surface of rim 152. Moreover, the height of the channel 531 may be dimensioned slightly larger than the thickness and depth of the rim 152 to facilitate engagement.

The distal end 516 of tissue guard 510 includes a plurality of scallop-like tabs 516a spaced-apart annularly thereabout. Scallop-like tabs 516a are configured engage an inner peripheral surface of body 112 of the access device 150 and are contoured or scalloped to generally mimic the shape thereof. The scallop-like tabs 516a are biased outwardly to maximize the opening at the distal end 516 of the tissue guard 510 and effectively secure the distal end 516 of the tissue guard 510 within access device 150 thereby facilitating surgical instrument access to the body cavity.

As mentioned above, lip 526 defines an annular channel therein configured to direct surgical exhaust therethrough to port 565 defined in an outer peripheral surface of lip 526. Lip 526 includes distal end 526a that extends inwardly therefrom towards lumen 518 to form annular channel 545 configured to direct surgical exhaust gas to port 565, respectively. One or more slits or passageways (passageways 113 of FIG. 1A) may be defined within the inner peripheral surface of distal end 526a that allow surgical gases passage into annular channel 545. As explained in more detail below, port 565 is configured to connect to an exhaust connection 776 of a fluid management or smoke evacuation system 700 (FIG. 1C). In other words, lip 526 is configured as generally hollow sleeves disposed proximate the inner peripheral surface of proximal end 514 of tissue guard 510 and is configured to direct evacuation fluids and smoke to the exhaust connection 776 and to the fluid management or smoke evacuation system 700.

Figure 3A:
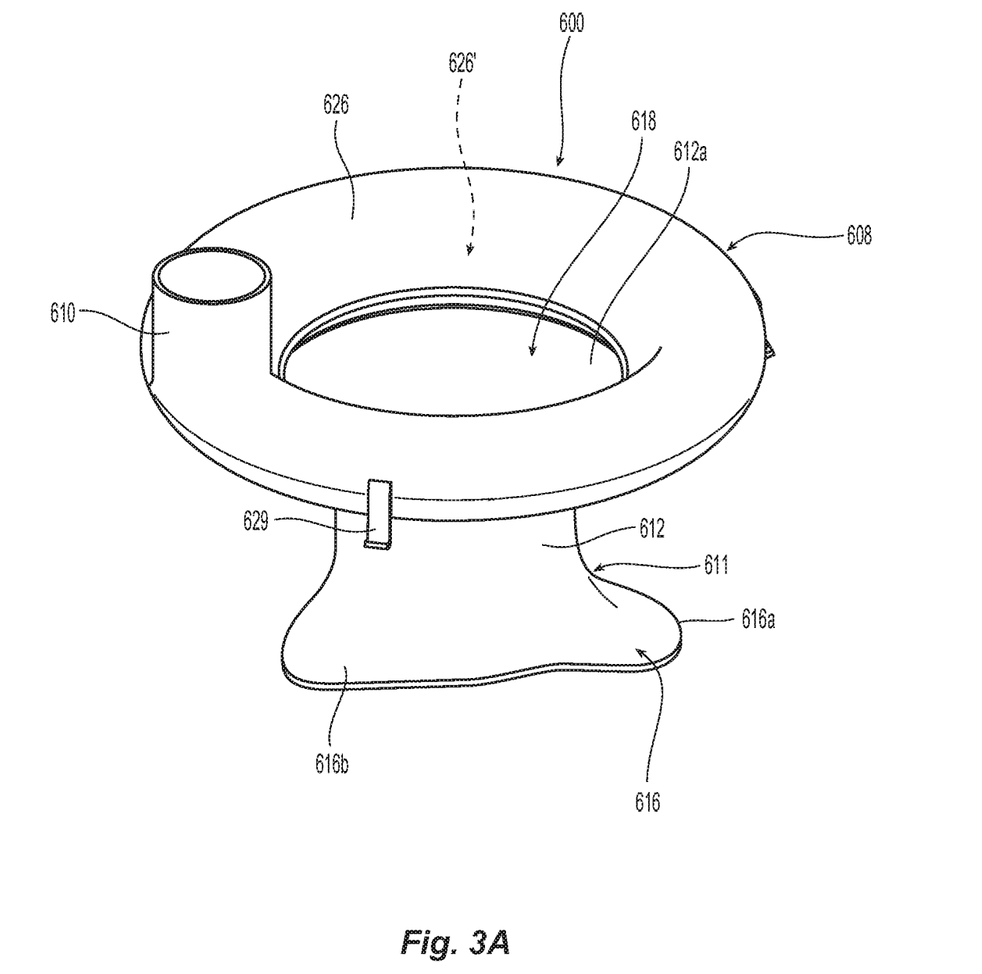
FIG. 3A is a top perspective view of one embodiment of a tissue guard for use with the access device in accordance with the present disclosure.
Figure 3B:
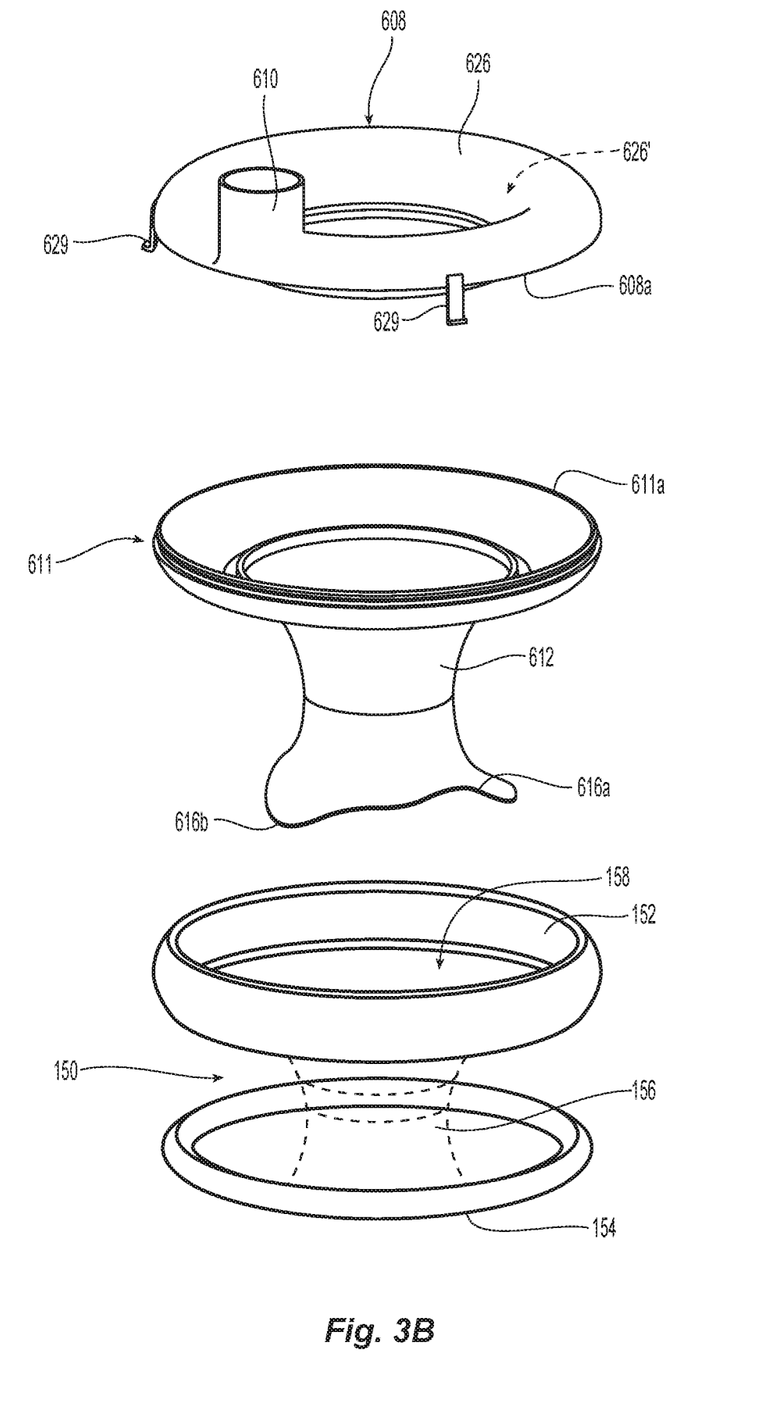
FIG. 3B is an exploded view of the tissue guard of FIG. 3A with an access device.

Turning to FIGS. 3A and 3B, one embodiment of a tissue guard is shown and is generally designated as reference numeral 600. Tissue guard 600 includes a body 612 and a proximal ring 626 that defines an annular smoke evacuation channel 626' therein configured to convey smoke, odors and miscellaneous gases from the operating cavity to a connection port 610 and then to smoke evacuation system 700 (FIG. 1C). More particularly, ring 626 is generally annular in shape and includes the connection port 610 that operably couples to tubing 710 of the smoke evacuation system 700. Guard 600 is configured to operably couple to the proximal rim 152 of access device 150 via one or more mechanically interfacing surfaces, e.g., fingers 629 described below.

Each finger 629 is configured to snap under rim 152 of the access device 150. More particularly, each finger 629 includes a flange 629a disposed at a distal end thereof that is configured to engage an underside of rim 152 to secure the tissue guard 600 in place. Fingers 629 are configured to flex upon insertion of the tissue guard 600 into access device 150 by virtue of rim 152 forcing flanges 629a and fingers 629 inwardly as the tissue guard 600 is inserted. Upon full insertion of the tissue guard 600 into access device 150, flanges 629a snap into place under rim 152 thereby locking the tissue guard 600 within access device 150. The fingers 629 are biased in the locked position. The flanges 629a extend outwardly relative to the proximal ring 152 and operably engage the underside of the proximal ring 152 when biased. Flanges 629a may be angled or include angled surfaces similar to the angles described above with respect to FIGS. 2A and 2B to both facilitate insertion and to facilitate engagement. In embodiments, each flange 629a may be disposed at an angle alpha (α) in the range of about 60 degrees to about 80 degrees relative to each finger 629.

Distal end 616 is generally oblong and includes a long petal 616a on one side thereof and a short petal 616b on an opposite side thereof to facilitate insertion of the tissue guard 600 into the access device 150 and an internal body cavity. Prior to insertion, short petal 616b may be inverted into body 612 such that only the long petal 616a remains exposed for insertion.

Short petal 616b may include a break line or snap point which is a point where the short petal 616b inverts on itself and into the body 612. In other words, once the user pushes the short petal 616b into the body 612 passed a certain point, the short petal 616b inverts onto itself and tucks within the inner periphery of the body 612. Likewise, when the user pushes the short petal 616b outwardly from the body 612 after insertion, the short petal 616b automatically reverses back or reverts to the expanded configuration to engage the underside of the tissue and secure the tissue guard 600.

Both the long petal 616a and the short petal 616b are configured in the shape of shoe-horns or duck-like flanges to facilitate insertion and retention thereof when engage against tissue "T". In other words, the shape of the petals 616a, 616b include a generally tapered, spoon-like distal edge to facilitate both insertion into an incision in tissue "T" (e.g., petal 616a) and retention against the tissue "T" once inserted.

In use, prior to insertion, the short petal 616b of the tissue guard 600 is initially inverted to reduce the profile of the tissue guard 600 and to facilitate insertion. The long petal 616a is then inserted into the incision and slipped through the incision in a manner to pry open the incision like a shoe-horn. Once seated within the incision with the proximal flange 626 flush against the external side of tissue "T", the surgeon inserts an instrument (or finger) into the tissue guard 600 to push and rotate the short petal 616b outwardly to engage the opposite side of tissue "T" within incision. This seats the tissue guard 600 within the access device 150 in a more balanced fashion and provides opposing retention for the tissue guard 600 therein. As mentioned above, the shoe-horn or duck-bill shape of the petals 616a, 616b facilitate retention of the tissue guard 600 within the access device 150 in the incision.

Figure 4:
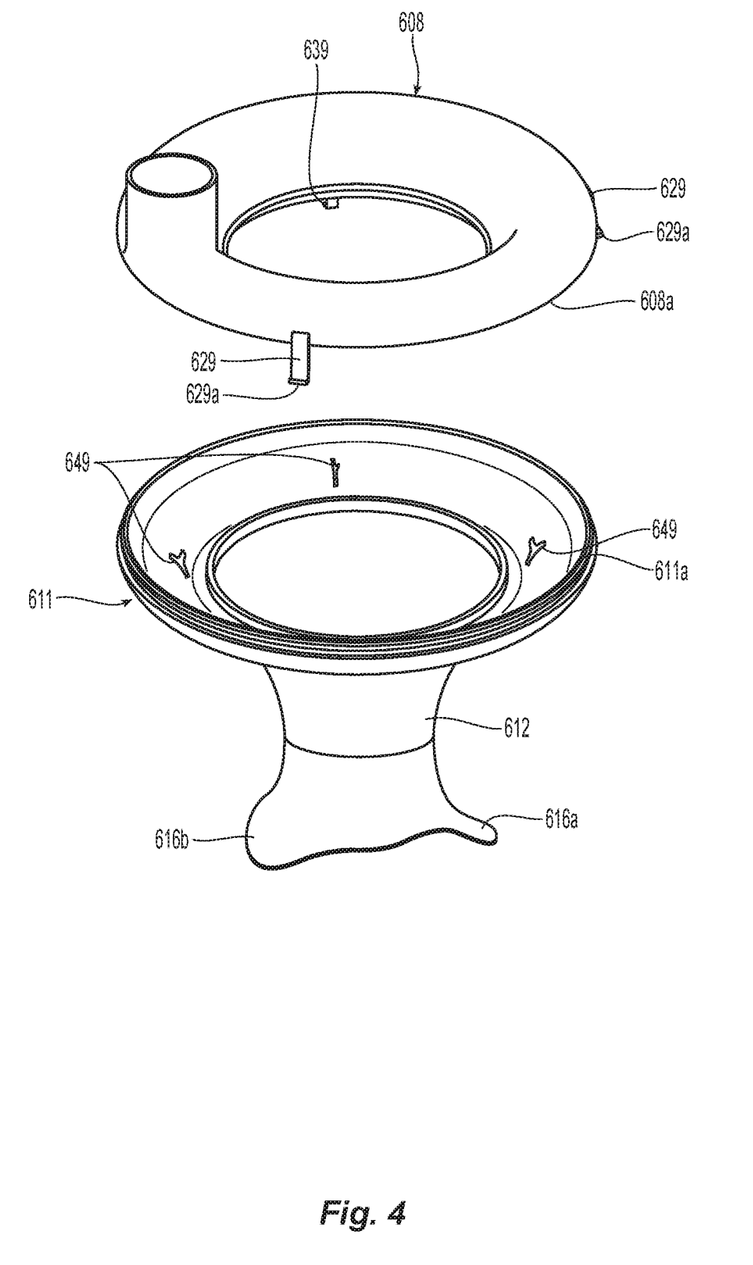
FIG. 4 is an exploded view of the tissue guard of FIG. 3A.
Figure 5A:
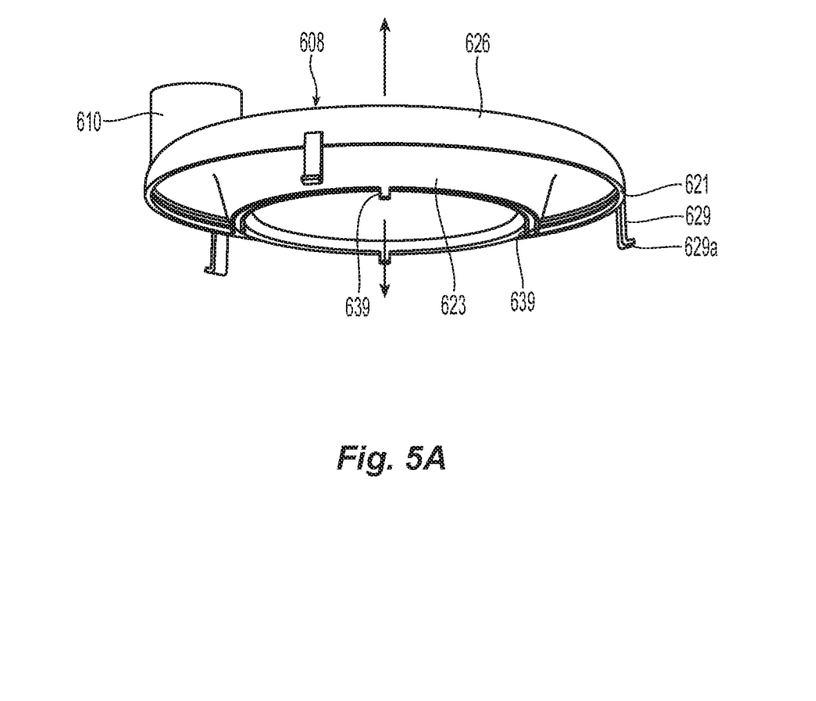
FIG. 5A is a bottom, perspective view of an upper portion of the tissue guard of FIG. 3A.
Figure 5B:
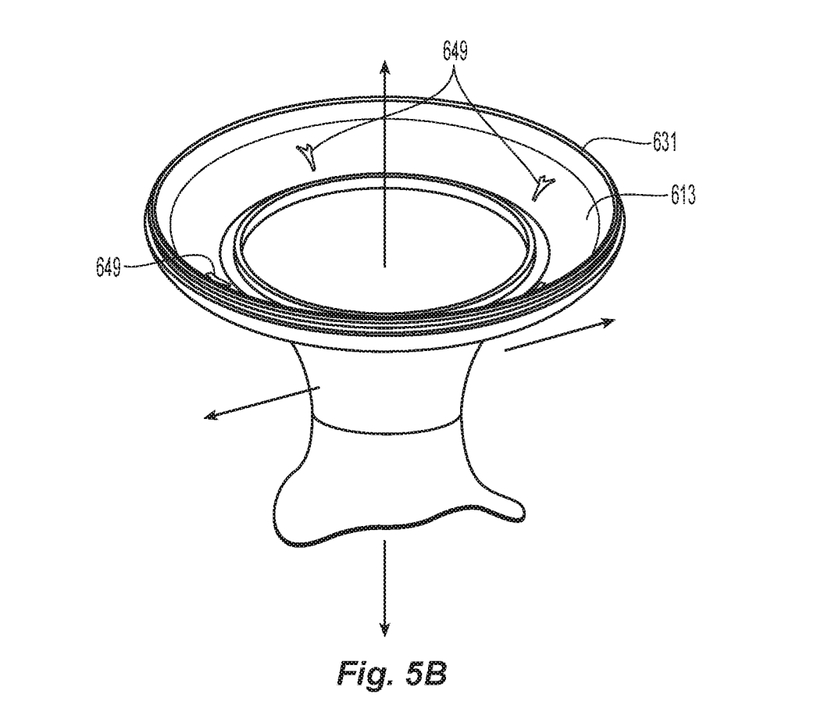
FIG. 5B is a top, perspective view of a lower portion of the tissue guard of FIG. 3A.

Turning back to FIGS. 3A-6B, tissue guard 600 includes an upper portion 608 and a lower portion 611 that mechanically engage one another to form the tissue guard 600. Upper portion 608 includes proximal rim 626, port 610 and the fingers 629 and lower portion includes body 612 and then distal end 616 of the tissue guard 600. Upper portion 608 also includes a series of female post snaps 639 disposed about a distal end of the inner peripheral surface 623 of the upper portion 608 that are configured to mechanically engage a corresponding series of male post snaps 649 disposed about an inner peripheral surface 613 of body 612 (See FIG. 4) upon assembly. More particularly, upon insertion of the lower portion 611 of the tissue guard 600 within the access device 150 as explained above, a distal rim 608a of the upper portion 608 is concentrically-aligned with a proximal rim 611a of the lower portion 611. The distal rim 608a includes a tongue 621 and groove 621a feature and the proximal rim 611a includes an opposite tongue 631 and groove 631a feature that are configured to mechanically engage one another (e.g., snap-fit) upon assertion.

Prior to engagement of the rims 608a, 611a, the female and male post snaps 639, 649, respectively, are aligned in vertical registration with one another. In a substantial simultaneous fashion, the female and male post snaps 639, 649, and the tongue and groove arrangements 621, 621a and 631, 631a of the rims 608a, 611a are then forced into engagement with one another in a snap-fit manner by pressing towards the arrows "A" and "B" (See FIGS. 6A and 6B). This locks the lower portion 611 and the upper portion 608 together and completes the smoke evacuation channel 626'. The fingers 629 are then engage to the underside of the annular rim 152 as described above and the tissue guard 600 is ready for use.

Figure 6A:
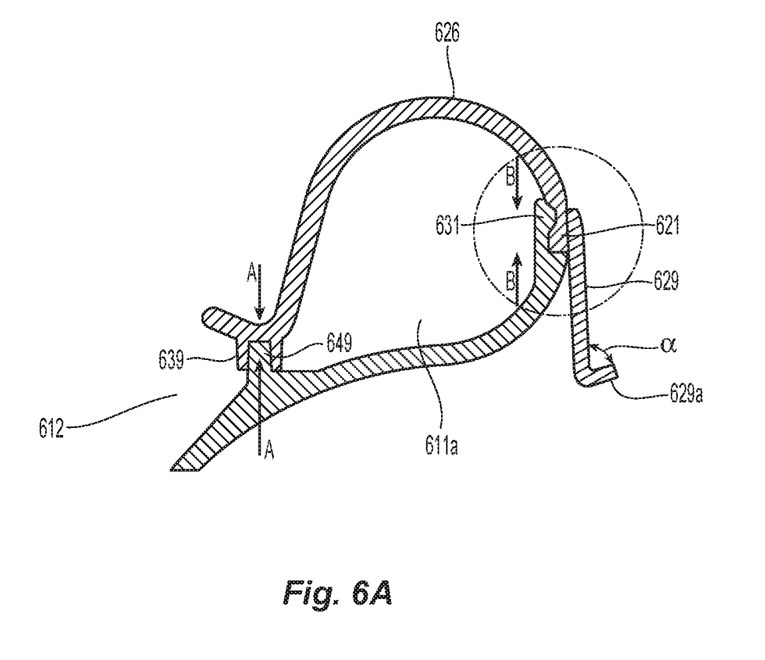
FIG. 6A is an enlarged, cut-away view showing the engagement of the upper and lower portions of the tissue guard of FIG. 3A.
Figure 6B:
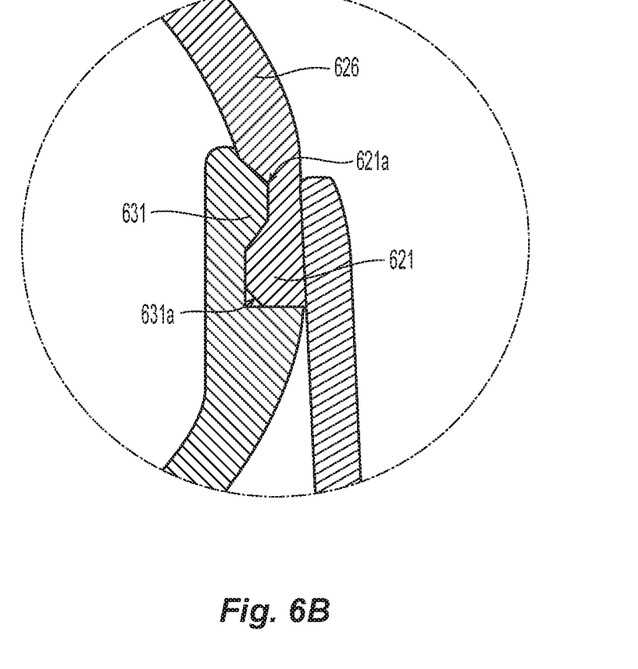
FIG. 6B is a greatly-enlarged, cut-away view showing the engagement of a rim of the upper portion and a rim of the lower portion of the tissue guard of FIG. 3A.

After use, the tongue and groove arrangements 621, 621a and 631, 631a of the rims 608a, 611a and the female and male post snaps 639, 649 may be separated in a similar fashion to facilitate removal of the tissue guard 600.

In embodiments, engagement or disengagement of the two mechanically-engaging features may be sequential versus simultaneous. Moreover, other mechanically-engaging features are envisioned which will accomplish the same or similar purpose.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue guard for use with a surgical access device, comprising:
   an upper portion including:
      a proximal ring including proximal and distal ends, the distal end including a first mechanical interface disposed therearound;
      a plurality of fingers extending about the proximal ring, each finger configured to mechanically engage a rim of an access device to secure the tissue guard thereon;
      an inner peripheral surface having an upper channel defined therein disposed in fluid communication with an operating cavity, the inner peripheral surface depending from the proximal ring; and
      a plurality of second mechanical interfaces disposed about a distal end of the inner peripheral surface;
   a lower portion including:
      an elongated body having proximal and distal ends, the proximal end including a corresponding first mechanical interface disposed therearound configured to, upon assembly, mechanically engage the first mechanical interface of the upper portion;
      a lower channel defined within the elongated body in vertical registration with the upper channel, the lower channel including a plurality of corresponding second mechanical interfaces disposed thereon configured to, upon assembly, engage the plurality of second mechanical interfaces of the upper portion; and a long petal and a short petal disposed at the distal end of the lower portion, the short petal configured to move between a first position wherein the short petal is disposed within the lower channel to facilitate insertion of the long petal within an incision and a second position wherein the short petal is extended relative to the lower channel and in substantial opposition to the long petal to facilitate retention of the tissue guard within the incision.

2. The tissue guard according to claim 1, wherein the first mechanical interface of the upper portion includes a tongue and groove and the first mechanical interface of the lower portion includes a tongue and groove configured to mechanically engage the tongue and groove of the upper portion.

3. The tissue guard according to claim 1, wherein the plurality second mechanical interfaces of the upper portion includes a male post snap and the plurality second mechanical interfaces of the lower portion includes a female post snap configured to mechanically engage the plurality of male post snaps of the upper portion.

4. The tissue guard according to claim 1, wherein each of the plurality of fingers of the upper portion includes a flange at a distal end thereof configured to engage an underside of the rim of the access device.

5. The tissue guard according to claim 4, wherein each flange of the plurality of fingers is disposed at an angle relative to each finger.

6. The tissue guard according to claim 4, wherein each flange of the plurality of fingers is disposed at an angle in the range of about 60 degrees to about 80 degrees relative to each finger.

7. The tissue guard according to claim 1, wherein the short petal is selectively invertable within the lower channel.

8. The tissue guard according to claim 1, wherein the long petal is shaped like a shoe horn and is configured to pry the incision open upon insertion therein.

9. The tissue guard according to claim 1, wherein after insertion of the long petal within the incision, the short petal is selectively extendible from the lower channel to engage tissue opposite the long petal to facilitate retention of the tissue guard.

10. A tissue guard for use with a surgical access device, comprising:
an upper portion including:
a proximal ring including proximal and distal ends, the distal end including a first mechanical interface disposed therearound;
a plurality of fingers extending about the proximal ring, each finger configured to mechanically engage an underside of a rim of an access device to secure the tissue guard thereon;
an inner peripheral surface having an upper channel defined therein disposed in fluid communication with an operating cavity, the inner peripheral surface depending from the proximal ring; and
a plurality of second mechanical interfaces disposed about a distal end of the inner peripheral surface;
a lower portion including:
an elongated body having proximal and distal ends, the proximal end including a corresponding first mechanical interface disposed therearound configured to, upon assembly, mechanically engage the first mechanical interface of the upper portion; and a lower channel defined within the elongated body in vertical registration with the upper channel, the lower channel including a plurality of corresponding second mechanical interfaces disposed thereon configured to, upon assembly, engage the plurality of second mechanical interfaces of the upper portion,
wherein the lower portion is configured for initial insertion within the access device and upper portion is subsequently engaged with the lower portion.

11. The tissue guard according to claim 10, wherein the first and second mechanical interfaces of the upper and lower portions are configured to engage in a substantially simultaneous manner.

12. The tissue guard according to claim 10, wherein the first and second mechanical interfaces of the upper and lower portions are configured to engage in a sequential manner.

13. The tissue guard according to claim 10, wherein the first and second mechanical interfaces of the upper and lower portions are configured to engage one another prior to engagement of the plurality of fingers of the upper portion with the access device.

14. A tissue guard for use with a surgical access device, comprising:
an upper portion including:
a proximal ring including proximal and distal ends, the distal end configured to operably engage an access device to secure the tissue guard within the access device;
an inner peripheral surface disposed in fluid communication with an operating cavity depending from the proximal ring and including a plurality of mechanical interfaces disposed about a distal end of the inner peripheral surface;
a lower portion including:
an elongated body having proximal and distal ends, the proximal end configured to, upon assembly, mechanically engage the upper portion; and
a lower channel defined within the elongated body including a plurality of corresponding mechanical interfaces disposed on the elongated body configured to, upon assembly, operably engage the plurality of mechanical interfaces of the upper portion, wherein the lower portion is configured for initial insertion within the access device and upper portion is subsequently engaged with the lower portion.

15. The tissue guard according to claim 14, wherein the mechanical interfaces of the upper and lower portions are configured to engage in a substantially simultaneous manner.

16. The tissue guard according to claim 14, wherein the mechanical interfaces of the upper and lower portions are configured to engage in a sequential manner.

17. The tissue guard according to claim 14, further comprising:
a long petal and a short petal disposed at the distal end of the lower portion, the short petal configured to move between a first position wherein the short petal is disposed within the lower channel to facilitate insertion of the long petal within an incision and a second position wherein the short petal is extended relative to the lower channel and in substantial opposition to the long petal to facilitate retention of the tissue guard within the incision.

18. The tissue guard according to claim 17, wherein the short petal is selectively invertable within the lower channel.

19. The tissue guard according to claim 17, wherein the long petal is shaped like a shoe horn and is configured to pry the incision open upon insertion into the incision.

20. The tissue guard according to claim 17, wherein, after insertion of the long petal within the incision, the short petal is selectively extendible from the lower channel to engage tissue opposite the long petal to facilitate retention of the tissue guard.

\* \* \* \* \*